United States Patent
Sicvol et al.

(10) Patent No.: US 7,967,821 B2
(45) Date of Patent: Jun. 28, 2011

(54) BREAK-OFF SCREW EXTENSION REMOVAL TOOLS

(75) Inventors: Christopher Sicvol, Boston, MA (US); Shawn D. Stad, Fall River, MA (US); Timothy Beardsley, Kingston, MA (US); Douglas Bireley, Barrington, RI (US); James J. Roveda, North Attleboro, MA (US); Anthony R. Carlone, Bristol, RI (US)

(73) Assignee: DePuy Spine, Inc., Raynham, MA (US)

( * ) Notice: Subject to any disclaimer, the term of this patent is extended or adjusted under 35 U.S.C. 154(b) by 1084 days.

(21) Appl. No.: 11/561,497

(22) Filed: Nov. 20, 2006

(65) Prior Publication Data

US 2008/0119850 A1    May 22, 2008

(51) Int. Cl.
*A61B 17/70* (2006.01)
(52) U.S. Cl. .............. 606/86 A; 606/264; 606/265
(58) Field of Classification Search ............. 606/86 A
See application file for complete search history.

(56) References Cited

U.S. PATENT DOCUMENTS

| | | | |
|---|---|---|---|
| 4,448,191 A | 5/1984 | Rodnyansky et al. | |
| 5,020,519 A | 6/1991 | Hayes et al. | |
| 5,242,443 A | 9/1993 | Kambin | |
| 5,520,689 A | 5/1996 | Schlapfer et al. | |
| 5,649,963 A * | 7/1997 | McDevitt | 606/232 |
| 5,720,751 A | 2/1998 | Jackson | |
| 5,772,661 A | 6/1998 | Michelson | |
| 5,910,141 A | 6/1999 | Morrison et al. | |
| 5,984,923 A | 11/1999 | Breard | |
| 5,989,255 A | 11/1999 | Pepper et al. | |
| 6,030,388 A | 2/2000 | Yoshimi et al. | |
| 6,059,786 A | 5/2000 | Jackson | |
| 6,183,472 B1 | 2/2001 | Lutz | |
| 6,226,548 B1 | 5/2001 | Foley et al. | |
| 6,235,028 B1 | 5/2001 | Brumfield et al. | |

(Continued)

FOREIGN PATENT DOCUMENTS

DE    202005007495    8/2005

(Continued)

OTHER PUBLICATIONS

Moss Miami, Brochure "Polyaxial Reduction Screw", 1998 DePuy AcroMed, Inc.

(Continued)

*Primary Examiner* — Eduardo C Robert
*Assistant Examiner* — Ellen C Hammond
(74) *Attorney, Agent, or Firm* — Nutter McClennen & Fish LLP

(57) ABSTRACT

The present invention provides minimally invasive devices and methods for delivering a spinal connector to one or more spinal anchor sites in a patient's spinal column. In one embodiment, a spinal implant and access device is provided that includes a U-shaped receiver member, a bone-engaging member, and an extension member. The U-shaped receiver member can have a recess formed therein that is adapted to seat a spinal connector. The bone-engaging member can extend distally from the receiver member and it can be adapted to engage bone to thereby mate the receiver member to bone. The extension member can extend proximally from the receiver member and it can include a frangible portion formed thereon that is adapted to break when a predetermined force is applied thereto thereby allowing at least a portion of the extension member to be separated from the receiver member.

12 Claims, 15 Drawing Sheets

U.S. PATENT DOCUMENTS

| | | | | |
|---|---|---|---|---|
| 6,258,090 | B1 | 7/2001 | Jackson | |
| 6,478,795 | B1* | 11/2002 | Gournay et al. | 606/246 |
| 6,485,491 | B1 | 11/2002 | Farris et al. | |
| 6,530,929 | B1 | 3/2003 | Justis et al. | |
| 6,648,888 | B1 | 11/2003 | Shluzas | |
| 6,660,006 | B2 | 12/2003 | Markworth et al. | |
| 6,740,086 | B2 | 5/2004 | Richelsoph | |
| 6,740,089 | B2 | 5/2004 | Haider | |
| 6,743,231 | B1 | 6/2004 | Gray et al. | |
| 6,802,844 | B2 | 10/2004 | Ferree | |
| 6,821,277 | B2 | 11/2004 | Teitelbaum | |
| 6,951,538 | B2 | 10/2005 | Ritland | |
| 7,008,422 | B2* | 3/2006 | Foley et al. | 623/17.16 |
| 7,008,424 | B2 | 3/2006 | Teitelbaum | |
| 7,011,660 | B2 | 3/2006 | Sherman et al. | |
| 7,160,300 | B2 | 1/2007 | Jackson | |
| 7,179,261 | B2 | 2/2007 | Sicvol et al. | |
| 7,186,255 | B2 | 3/2007 | Baynham et al. | |
| 7,188,626 | B2 | 3/2007 | Foley et al. | |
| 7,250,052 | B2 | 7/2007 | Landry et al. | |
| 7,261,714 | B2 | 8/2007 | Richelsoph | |
| 7,491,218 | B2* | 2/2009 | Landry et al. | 606/246 |
| 7,527,638 | B2 | 5/2009 | Anderson et al. | |
| 2002/0087188 | A1* | 7/2002 | Pedlick et al. | 606/232 |
| 2002/0161368 | A1 | 10/2002 | Foley et al. | |
| 2003/0060826 | A1* | 3/2003 | Foley et al. | 606/61 |
| 2003/0130659 | A1 | 7/2003 | Haider | |
| 2003/0199873 | A1 | 10/2003 | Richelsoph | |
| 2003/0199884 | A1 | 10/2003 | Davison et al. | |
| 2003/0225408 | A1 | 12/2003 | Nichols et al. | |
| 2003/0229347 | A1 | 12/2003 | Sherman et al. | |
| 2004/0014326 | A1 | 1/2004 | Din | |
| 2004/0039384 | A1 | 2/2004 | Boehm et al. | |
| 2004/0049191 | A1 | 3/2004 | Markworth et al. | |
| 2004/0138662 | A1 | 7/2004 | Landry et al. | |
| 2004/0143265 | A1* | 7/2004 | Landry et al. | 606/61 |
| 2004/0162560 | A1* | 8/2004 | Raynor et al. | 606/73 |
| 2004/0172022 | A1 | 9/2004 | Landry et al. | |
| 2004/0193160 | A1 | 9/2004 | Richelsoph | |
| 2004/0215190 | A1 | 10/2004 | Nguyen et al. | |
| 2004/0267275 | A1 | 12/2004 | Cournoyer et al. | |
| 2005/0010219 | A1 | 1/2005 | Dalton | |
| 2005/0010221 | A1 | 1/2005 | Dalton | |
| 2005/0021031 | A1 | 1/2005 | Foley et al. | |
| 2005/0033299 | A1 | 2/2005 | Shluzas | |
| 2005/0038434 | A1 | 2/2005 | Mathews | |
| 2005/0065517 | A1 | 3/2005 | Chin | |
| 2005/0080418 | A1 | 4/2005 | Simonson et al. | |
| 2005/0085813 | A1 | 4/2005 | Spitler et al. | |
| 2005/0131408 | A1* | 6/2005 | Sicvol et al. | 606/61 |
| 2005/0131421 | A1 | 6/2005 | Anderson et al. | |
| 2005/0131422 | A1 | 6/2005 | Anderson et al. | |
| 2005/0137594 | A1 | 6/2005 | Doubler et al. | |
| 2005/0154389 | A1 | 7/2005 | Selover et al. | |
| 2005/0171540 | A1 | 8/2005 | Lim et al. | |
| 2005/0182407 | A1 | 8/2005 | Dalton | |
| 2005/0182410 | A1 | 8/2005 | Jackson | |
| 2005/0192570 | A1* | 9/2005 | Jackson | 606/61 |
| 2005/0192579 | A1 | 9/2005 | Jackson | |
| 2005/0192589 | A1 | 9/2005 | Raymond et al. | |
| 2005/0215999 | A1 | 9/2005 | Birkmeyer et al. | |
| 2005/0228380 | A1 | 10/2005 | Moore et al. | |
| 2005/0234449 | A1 | 10/2005 | Aferzon | |
| 2005/0261687 | A1 | 11/2005 | Garamszegi et al. | |
| 2005/0273101 | A1* | 12/2005 | Schumacher | 606/61 |
| 2005/0277934 | A1 | 12/2005 | Vardiman | |
| 2005/0283245 | A1* | 12/2005 | Gordon et al. | 623/17.15 |
| 2006/0009777 | A1 | 1/2006 | Lim et al. | |
| 2006/0025771 | A1 | 2/2006 | Jackson | |
| 2006/0036244 | A1 | 2/2006 | Spitler et al. | |
| 2006/0036252 | A1 | 2/2006 | Baynham et al. | |
| 2006/0036255 | A1 | 2/2006 | Pond et al. | |
| 2006/0058794 | A1 | 3/2006 | Jackson | |
| 2006/0069391 | A1 | 3/2006 | Jackson | |
| 2006/0084980 | A1 | 4/2006 | Melkent et al. | |
| 2006/0084993 | A1 | 4/2006 | Landry et al. | |
| 2006/0089643 | A1 | 4/2006 | Mujwid | |
| 2006/0111712 | A1* | 5/2006 | Jackson | 606/61 |
| 2006/0111713 | A1* | 5/2006 | Jackson | 606/61 |
| 2006/0111714 | A1 | 5/2006 | Foley | |
| 2006/0142761 | A1 | 6/2006 | Landry et al. | |
| 2006/0149238 | A1 | 7/2006 | Sherman et al. | |
| 2006/0184178 | A1 | 8/2006 | Jackson | |
| 2006/0200135 | A1 | 9/2006 | Sherman et al. | |
| 2006/0229614 | A1 | 10/2006 | Foley et al. | |
| 2006/0247630 | A1 | 11/2006 | Iott et al. | |
| 2006/0264942 | A1 | 11/2006 | Lim et al. | |
| 2006/0293664 | A1 | 12/2006 | Schumacher | |
| 2006/0293680 | A1 | 12/2006 | Jackson | |
| 2007/0018549 | A1 | 1/2007 | Chai et al. | |
| 2007/0049931 | A1 | 3/2007 | Justis et al. | |
| 2007/0106123 | A1 | 5/2007 | Gorek et al. | |
| 2007/0179502 | A1 | 8/2007 | Raynor et al. | |
| 2007/0185491 | A1 | 8/2007 | Foley et al. | |
| 2007/0191840 | A1 | 8/2007 | Pond et al. | |
| 2007/0198015 | A1 | 8/2007 | Foley et al. | |
| 2007/0288002 | A1* | 12/2007 | Carls et al. | 606/61 |
| 2007/0288026 | A1 | 12/2007 | Shluzas | |
| 2007/0299443 | A1 | 12/2007 | DiPoto et al. | |
| 2008/0015584 | A1 | 1/2008 | Richelsoph | |
| 2008/0082103 | A1 | 4/2008 | Hutton et al. | |
| 2008/0114403 | A1 | 5/2008 | Kuester et al. | |
| 2008/0119849 | A1 | 5/2008 | Beardsley et al. | |
| 2008/0125817 | A1 | 5/2008 | Arnett et al. | |
| 2008/0262318 | A1 | 10/2008 | Gorek et al. | |
| 2008/0300638 | A1 | 12/2008 | Beardsley et al. | |

FOREIGN PATENT DOCUMENTS

| | | | |
|---|---|---|---|
| WO | 9311715 | A1 | 6/1993 |
| WO | 2005006948 | A2 | 1/2005 |
| WO | 2006042189 | A2 | 4/2006 |

OTHER PUBLICATIONS

Moss Miami Spinal System, Brochure "Polyaxial Screw" Dec. 2000.

Synthes Spine, Brochure "USS Fracture System Technique Guide" Sep. 2004.

International Preliminary Report on Patentability, PCT/US2007/023415, Jun. 15, 2009.

Zimmer Spine, Silhouelte Spinal Fixation System, Catalog, Mar., 2005, 6 pgs.

International Search Report for Application No. PCT/US2007/014258 dated Dec. 28, 2007.

* cited by examiner

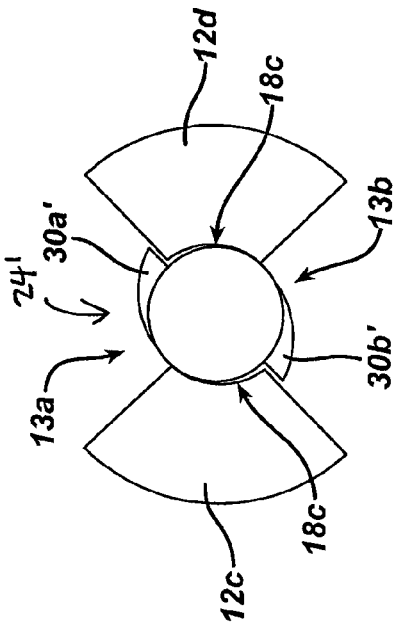
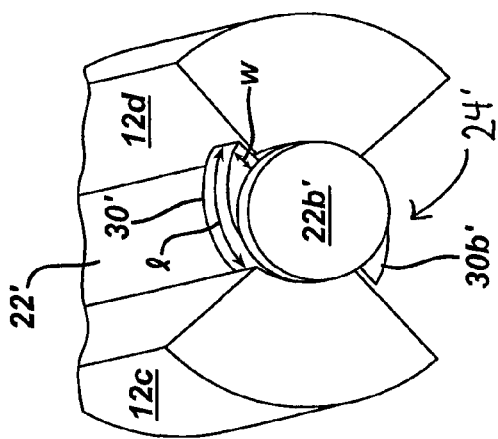
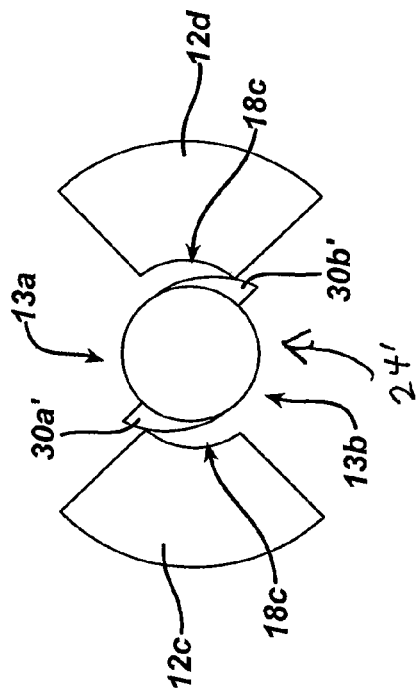

BREAK-OFF SCREW EXTENSION REMOVAL TOOLS

FIELD OF THE INVENTION

The present invention relates to tools for use in spinal surgery, and in particular to minimally invasive methods and devices for introducing a spinal connector to one or more spinal anchor sites within a patient's spine.

BACKGROUND OF THE INVENTION

For a number of known reasons, spinal fixation devices are used in orthopedic surgery to align and/or fix a desired relationship between adjacent vertebral bodies. Such devices typically include a spinal connector, such as a relatively rigid fixation rod, that is coupled to adjacent vertebrae by attaching the connector to various anchoring devices, such as hooks, bolts, wires, or screws. The connector can have a predetermined contour that has been designed according to the properties of the target implantation site, and once installed, the instrument holds the vertebrae in a desired spatial relationship, either until healing or spinal fusion has taken place, or for some longer period of time.

Spinal connectors can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a receiving element, usually in the form of a U-shaped head. A set-screw, plug, or similar type of fastening mechanism is used to lock the spinal connector, e.g., a spinal rod, into the receiving head of the pedicle screw. In use, the shank portion of each screw is threaded into a vertebra, and once properly positioned, a rod is seated through the receiving member of each screw and the rod is locked in place by tightening a cap or other fastener mechanism to securely interconnect each screw and the spinal rod.

Minimally invasive devices and methods for implanting spinal fixation devices are advantageous because such devices and methods utilize few incisions for introducing and implanting anchoring devices and spinal connectors at a target site within a patient's spine. Such procedures offer advantages over invasive techniques because they reduce the amount of damage to surrounding tissue and muscle and the amount of time required to complete the procedure.

Accordingly, there is a need for improved minimally invasive devices and methods for introducing a spinal connector into a patient's spine.

SUMMARY OF THE INVENTION

The present invention provides minimally invasive devices and methods for implanting a spinal anchor in bone, for percutaneously delivering various tools and implants to the spinal anchor through an extension coupled thereto, and for removing the extension coupled to the spinal anchor. In one embodiment, a spinal implant and access device is provided that includes a U-shaped receiver member, a bone-engaging member, and an extension member. The U-shaped receiver member can have a recess formed therein that is adapted to seat a spinal connector, such as a spinal rod. In one exemplary embodiment, the receiver member can have a maximum outer diameter that is substantially the same as a maximum outer diameter of the extension member. The bone-engaging member can extend distally from the receiver member and it can be adapted to engage bone to thereby mate the receiver member to bone. A variety of configurations are available for the bone-engaging member, for example, in one embodiment the bone-engaging member can be a threaded shank such as a bone screw.

As indicated above, the access device can include an extension member. The extension member can extend proximally from the receiver member and it can have a lumen extending therethrough. Although a variety of shapes and sizes are available for the extension member in an exemplary embodiment, the extension member has a length that is adapted to span through a skin surface in a patient to the U-shaped receiver member when the bone engaging member is implanted in a vertebra. The extension member can also include a frangible portion formed thereon that is adapted to break when a predetermined force is applied thereto thereby allowing at least a portion of the extension member to be separated from the receiver member. In one embodiment, the extension member can include a proximal end and a distal end that is coupled to the receiver member. The frangible portion can be formed adjacent to the distal end.

The extension member can also have a variety of configurations. For example, in one embodiment, the extension member can include first and second opposed extension arms that extend proximally from the U-shaped receiver member and that are separated by opposed slots that extend between the arms. The opposed slots can extend from the proximal end to the distal end or the first and second extension arms can be coupled to one another at least one location located proximal to the frangible portion. In another embodiment, the extension member can be a hollow elongate tube. The hollow elongate tube can include opposed slots that extend from a distal end of the tube and that terminate distal to a proximal end of the tube. Various configurations are also available for the frangible portion of the extension member. For example, in one embodiment, the frangible portion can include an annular groove formed around the extension member.

In another embodiment, a removal tool is provided. Although a variety of configurations are available for the removal tool, in an exemplary embodiment the tool can include an elongate member having a proximal portion that is adapted to be positioned adjacent to a skin incision and a distal portion that is adapted to be positioned adjacent to a vertebra and to be received within a lumen formed in an extension member of a spinal anchor. The distal portion can include an engagement mechanism that is adapted to engage an inner surface of the extension member of the spinal anchor and to apply a radially directed force to the extension member disposed therearound to break at least a portion of the extension member apart from the spinal anchor. The engagement mechanism can have a variety of configurations. For example, in one embodiment, the engagement mechanism can be a cam formed on a distal portion of the elongate member. In another embodiment, the engagement mechanism can be a set screw formed on a distal portion of the elongate member. The set screw can have a proximal threaded portion with an outer diameter that is greater than an outer diameter of a distal threaded portion. The removal tool can also include a handle disposed on a proximal portion that is adapted to rotate the elongate member to cause the engagement mechanism to apply a radially directed force to an extension member that is disposed therearound.

Exemplary spinal systems are also provided. In one embodiment, system can include a spinal anchor and a removal tool. The spinal anchor can be adapted to be implanted in bone and it can have a receiver member with a recess formed therein for seating a spinal connector. An extension member can be frangibly coupled to the receiver member and it can be adapted to span through a skin surface in a patient to the receiver member when the receiver member is coupled to a vertebra. A variety of configurations are available for the extension member and the removal tool, including those discussed above.

Methods for implanting a spinal anchor and removing a percutaneous access device from a spinal anchor are also provided. In one embodiment, the method can include percutaneously delivering a spinal anchor to a vertebra, advancing a spinal connector through an extension member that is frangibly attached to the spinal anchor, and separating the extension member from the spinal anchor. Advancing the spinal connector through the extension member can generally include advancing the connector in a first orientation substantially parallel to a longitudinal axis of the extension member and manipulating the connector to extend in a second orientation angled with respect to the first orientation to position the connector in relation to the spinal anchor. In one embodiment, the spinal connector can extend substantially parallel to a patient's spinal column in the second orientation. A variety of techniques can be used to separate the extension member from the spinal anchor. For example, removing the percutaneous access device from the spinal anchor can generally include inserting an elongate member into a lumen formed through the percutaneous access device and actuating the elongate member to cause the elongate member to apply a radially directed force to an inner surface of the access device to break at least a portion of the device away from the spinal anchor. In one exemplary embodiment, actuating the elongate member can include rotating the elongate member such that an engagement mechanism disposed on a distal portion of the member engages and applies the radially directed force to an inner surface of the access device. The elongate member can be rotated by applying a force to a handle disposed on a proximal end of the elongate member.

BRIEF DESCRIPTION OF THE DRAWINGS

The invention will be more fully understood from the following detailed description taken in conjunction with the accompanying drawings, in which:

FIG. 3A is a perspective view of a removal tool according to another embodiment of the present invention;

FIG. 3B is a cross-sectional view of the removal tool shown in FIG. 3A disposed within the extension member of the device of FIG. 1A;

FIG. 3C is a cross-sectional view of the removal tool and extension member shown in FIG. 3B showing the tool applying a force to an inner surface of the extension member;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides minimally invasive methods and devices for introducing a spinal connector into a surgical site in a patient's spinal column. In general, a spinal implant and access device is provided for creating a minimally invasive pathway from a skin incision to a spinal anchor site for delivering various tools and devices to the spinal anchor site. In an exemplary embodiment, the access device can be in the form of an extension member that is mated to or formed on and extends proximally from a spinal anchor. The extension member can be used to implant the spinal anchor, and, once the anchor is implanted, to manipulate the spinal anchor from outside of the patient's body as well as to provide a pathway through a skin surface to the spinal anchor for introducing various tools and spinal system components, such as spinal connectors, fasteners, installation tools, and removal tools. The extension member can also be adapted to be easily detached from or broken off of the spinal anchor once the procedure is complete. Such a configuration eliminates the steps of assembling, disassembling, and cleaning which are currently required for conventional screw extensions.

Figure 1A:
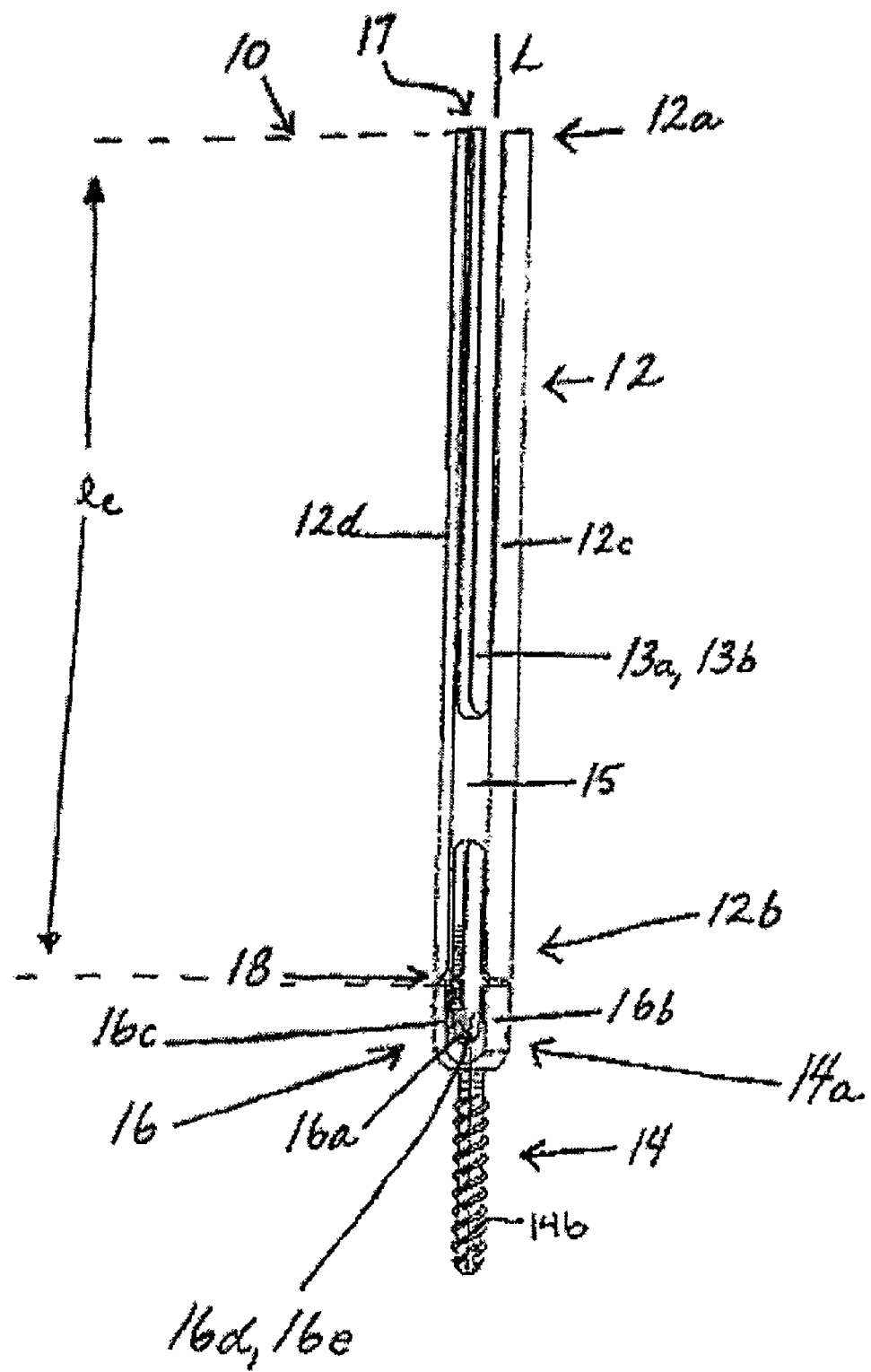
FIG. 1A is a perspective view of a spinal implant and access device having an extension frangibly coupled to a spinal anchor according to one embodiment of the present invention.

FIG. 1A illustrates one exemplary embodiment of a spinal implant and access device 10 having an extension member 12 that is mated to a spinal anchor 14. As shown, the anchor 14 includes a U-shaped receiver member 16 and a bone-engaging member 14b that extends distally from the receiver member 16. The U-shaped receiver member 16 can have a recess 16a formed therein that is adapted to seat a spinal connector, such as a spinal rod. The bone-engaging member 14b can extend distally from the receiver member 16 and it can be adapted to engage bone such that it is effective to mate the receiver member 16 to bone. The extension member 12 can include a distal end 12b that is mated to and extends proximally from the receiver member 16. In use, the extension member 12 can define a pathway from a skin incision in a patient to the spinal anchor, which can be implanted in a vertebra of a spine. In an exemplary embodiment, the extension member 12 can be removably mated to the receiver member 16 to allow at least a portion of the extension member 12 to be separated from the receiver member 16.

The anchor can have a variety of configurations. In the embodiment shown in FIG. 1A, the anchor 14 is in the form of a spinal screw. As shown, the spinal screw 14 includes a distal bone-engaging member 14b, e.g., a threaded shank, and a proximal U-shaped receiver member 16 that is adapted to seat a spinal connector, such as a rigid or dynamic spinal rod. The U-shaped receiver member 16 can include opposed arms 16b, 16c having cut-outs 16d, 16e formed therein that define the U-shaped recess 16a. The bone-engaging member 14b can be fixedly attached to the receiver member 16 to form a monoaxial screw, or alternatively the bone-engaging member 14b can be configured as a polyaxial screw that is rotatably disposed through an opening formed in the distal end of the receiver member 16 to allow rotation of the bone-engaging member 14b with respect to the receiver member 16. A variety of techniques known in the art can be used to allow rotation of the receiver member 16 with respect to the bone-engaging member 14b. A person skilled in the art will appreciate that a variety of other anchors can be used with the devices and methods of the present invention, including, for example, spinal hooks, bolts, and wires.

The extension member 12 that is coupled to the anchor 14 can also have a variety of configurations. In the illustrated embodiment, the extension member 12 extends proximally from the receiver member 16 and defines a lumen 17 extending therethrough. In particular, a distal end of opposed arms 12c, 12d of the extension member 12 can be mated to or integrally formed with and can extend proximally from a proximal end of the opposed arms 16b, 16c of the receiver member 16. As will be discussed in more detail below, this will allow opposed slots 13a, 13b in the extension member 12 to align with the opposed cut-outs 16d, 16e in the receiver member 16. The inner lumen 17 of the extension member 12 can define a longitudinal axis L that extends between proximal and distal ends 12a, 12b of the extension member 12. The size of the extension member 12 can vary depending on the intended use, but in an exemplary embodiment it has a length that allows the proximal end 12a of the extension member 12 to be positioned outside the patient's body, while the distal end 12b of the extension member 12 is coupled to the spinal anchor 14 which is implanted in a vertebra in a patient's spine. More particularly, the extension member 12 can have a length that allows the extension member 12 to span through the skin surface to the receiver member 16 when the bone engaging member is fully implanted in a vertebra, and the receiver member 16 is positioned adjacent to the vertebrae, e.g., the bottom surface of the receiver member 16 is in contact with or within about 1 mm to 2 mm of the vertebra. Such a configuration is particularly advantageous as it allows the extension member 12 to be used to introduce and facilitate positioning of various tools and devices therethrough, and it also allows the extension member 12 to be used to manipulate the anchor from outside of the patient's body. The length $l_e$ of the extension member 12 is illustrated in FIG. 1A, and is measured from the proximal-most end of the extension member 12 to the proximal end of the receiver member 16, i.e., to a frangible portion 18 that couples the extension member to the U-shaped receiver member 16 as will be discussed in more detail below. In an exemplary embodiment, the length $l_e$ is greater than about 25 mm, and more preferably is greater than about 55 mm. Thus, in such embodiments, the length of the extension member 12 and the receiver member 16 (which can be approximately 15 mm from the proximal-most end to the bottom or distal end), can be greater than about 40 mm, and more preferably greater than about 70 mm. Exemplary lengths $l_e$ of the extension member 12 range from 85 mm to 185 mm (100 mm to 200 mm with the receiver member), and more preferably from 135 mm to 175 mm (150 mm to 190 mm with the receiver member). In certain exemplary embodiments, the extension member can have a length $l_e$ of about 145 mm (160 mm with the receiver member) where the extension member has an open configuration, as will be discussed in more detail below, and a length $l_e$ of about 165 mm (180 mm with the receiver member) where the extension member has a closed configuration.

The extension member 12 can also be adapted to provide a minimally invasive pathway for the delivery of various implants and devices. In an exemplary embodiment, shown in FIG. 1C, the extension member 12 has inner and outer diameters $d_i$, $d_o$ that are substantially the same as the inner and outer diameters $d_{ri}$, $d_{ro}$ of the receiver member 16. The matching inner diameters will allow spinal connectors, fasteners, and other implants and devices to be inserted therethrough and coupled to the receiver member 16, and the matching outer diameters will allow a relatively small incision to be used to introduce the spinal implant and access device 10 into the body. It will also allow the extension member 12 and the anchor 14 to be introduced through a cannula or other access port, if necessary.

Figure 1B:
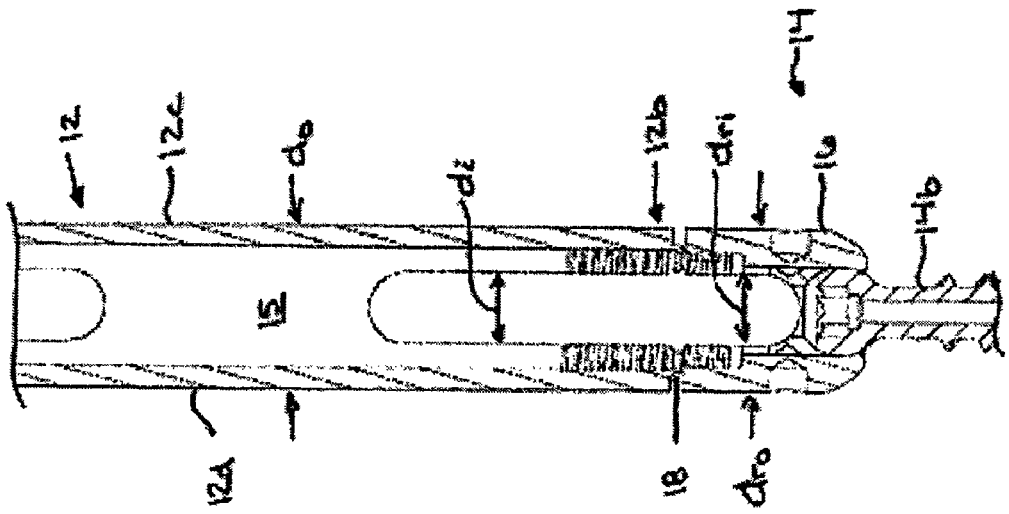
FIG. 1B is an enlarged perspective view of the frangible portion of the spinal implant and access device shown in FIG. 1A.
Figure 1C:
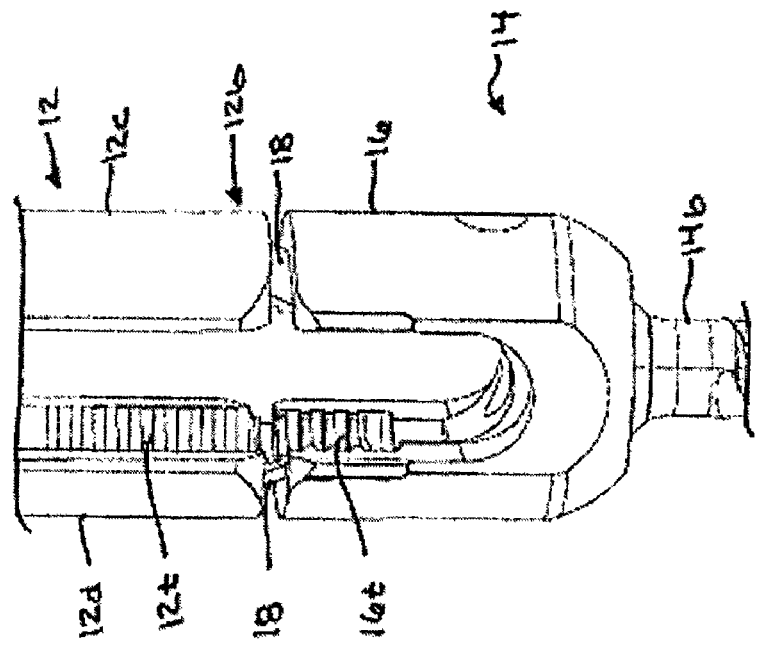
FIG. 1C is a cross-sectional view of a portion of the spinal implant and access device of FIG. 1A.
Figure 1D:
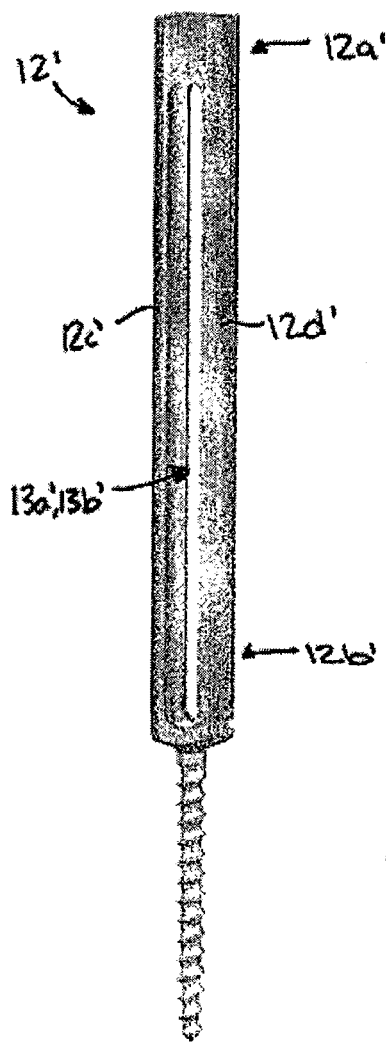
FIG. 1D is a perspective view of another embodiment of an extension member having a closed configuration for use with a spinal anchor and access device.

As indicated above, the extension member 12 can also include cut-outs or slots to facilitate the introduction of tools, spinal connectors, and other implants therethrough. A variety of configurations are available for the cut-outs. For example, as shown in FIG. 1A, the extension member 12 can include opposed slots 13a, 13b that extend between and separate the first and second opposed extension arms 12c, 12d that extend proximally from the U-shaped receiver member 16. The opposed slots 13a, 13b can extend from the proximal end 12a to the distal end 12b, such that the extension member 12 has an open configuration, or the first and second extension arms 12c, 12d can be coupled to one another at one or more locations along the length thereof, such that the extension member 12 has a closed configuration. FIGS. 1A and 1C illustrate the extension having a closed configuration, in which the first and second extension arms 12c, 12d are coupled to one another by a web or connector 15 located distal to the midpoint of the extensions 12c, 12d and proximal to a frangible portion 18, which will be discussed in more detail below. In use, the slot(s) 13a, 13b can be configured to allow various implants and devices to be passed therethrough. Thus, each slot 13a, 13b preferably has a width that is sufficient to accommodate the size of an implant or device to be passed therethrough. In another embodiment of an extension having a closed configuration, as shown in FIG. 1D, the first and second extension arms 12c', 12d' can be coupled to one another at the proximal end 12a' of the extension member 12'. Such a configuration resembles a hollow elongate tube having slots 13a', 13b' formed in the sidewalls thereof and extending proximally from the distal end 12b' thereof and terminating distal to the proximal end 12a' of the extension member 12'.

Figure 1E:
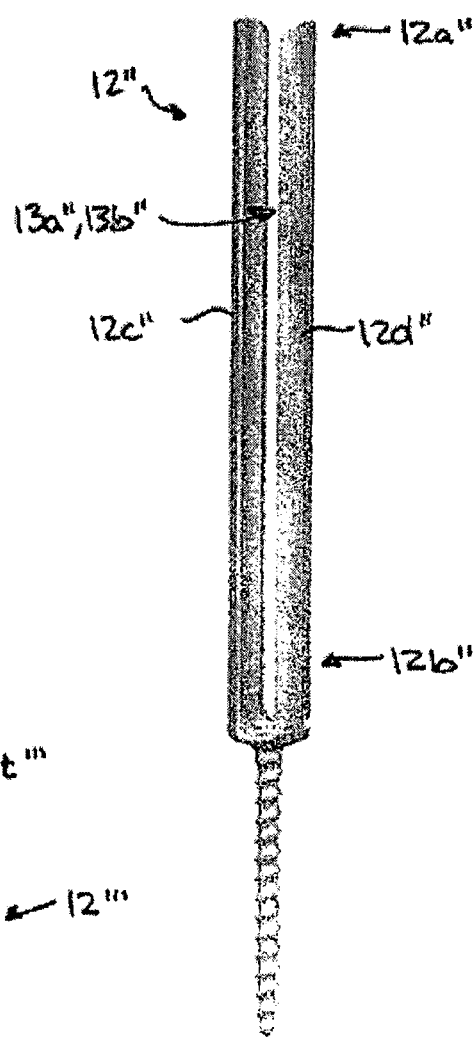
FIG. 1E is a perspective view of another embodiment of an extension member having an open configuration for use with a spinal anchor and access device.

Alternatively, the extension member can have an open configuration. This is illustrated in FIG. 1E, which shows an extension member 12" having first and second extension arms 12c", 12d" that are separated by slots 13a", 13b" that extend from the distal end 12b" of the extension member 12" and that extend through the entire proximal portion of the extension member 12" such that the proximal end 12a" of each arm 12c", 12d" is separated from one another. Accordingly, the quantity, shape, and size of the slot(s) 13a, 13b can vary. A person skilled in the art will appreciate that the extension member 12 can include any number of sidewall openings having any shape that is sufficient to allow desired implants and devices to be passed therethrough.

Figure 1F:
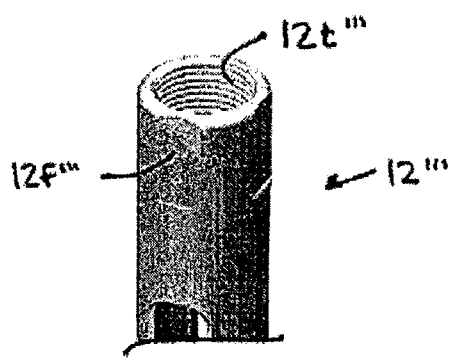
FIG. 1F is a perspective view of another embodiment of a proximal end of an extension member having threads formed therein and flats formed on an external surface thereof.

The extension member 12 can also include other features to facilitate use of the device. For example, in another embodiment, shown in FIG. 1F, the extension member 12'" includes threads 12t'" formed in a proximal portion of the extension member 12'" for mating with corresponding threads formed on a driver tool, reduction device, or other delivery device. The threads 12t'" will facilitate advancement of the delivery device through the extension member 12'". For example, the threads 12t'" can mate with corresponding threads on a rod reduction device to allow the rod reduction device to reduce a spinal rod or other spinal connector into the receiver member of the anchor. While FIG. 1F illustrates threads 12t'" formed within the proximal end of the extension member 12'", the threads 12t'" can be formed at any location along the length of the extension member 12'". For example, threads can be formed within the connector 15 (FIG. 1C) and around the circumference of the inner lumen of the extension member 12. As further shown in FIG. 1F, the extension member 12'" can also or alternatively include one or more flats 12f'" formed on an external surface thereof for use with external devices, such as a rod stabilizer. A person skilled in the art will appreciate that the extension member can have various other configurations to facilitate use with other delivery tools and/or fastening elements.

Referring back to FIGS. 1A-1C, as indicated above the extension member 12 can be removably coupled to the receiver member 16. In an exemplary embodiment, the distal end 12b of the extension member 12 is integrally formed with the receiver member 16, i.e., the extension member 12 and receiver member 16 have a unitary configuration. A frangible portion 18, best shown in FIG. 1A, can be formed on the extension member 12 to allow the extension member 12 to be frangibly separated from the receiver member 16. The frangible portion can be formed at various locations along the extension member 12, but in an exemplary embodiment the frangible portion 18 is located adjacent to the distal end 12b of the extension member 12. The frangible portion 18 can be adapted to break when a predetermined force is applied thereto thereby allowing at least a portion of the extension member 12 to be separated from the receiver member 16. A variety of techniques can be used to form a frangible portion 18. For example, in one embodiment shown in FIGS. 1A-1B, the frangible portion 18 can be formed by a reduced diameter region or thinned region of material formed between the extension member 12 and the receiver member 16. Other configurations for the frangible portion 18 can include webbing, an annular grooved formed in an outer or inner surface of the extension member 12, or other techniques known in the art. A variety of materials, including both plastics and metals, can be used for the frangible portion 18, and the frangible portion 18 need not be made from the same material used for the anchor 14 or extension member 12. By way of non-limiting example, the anchor 14 can be made from a metallic material, such as stainless steel, and the frangible portion 18 and extension member 12 can be formed from a plastic. Such a configuration allows the extension member 12 and frangible portion 18 to act as insulators during neuromonitoring. In use, the frangible portion 18 can provide a weak spot in the extension member 12 to allow the extension member 12 to be separated from the receiver member 16 when a predetermined force is applied thereto.

Figure 2A:
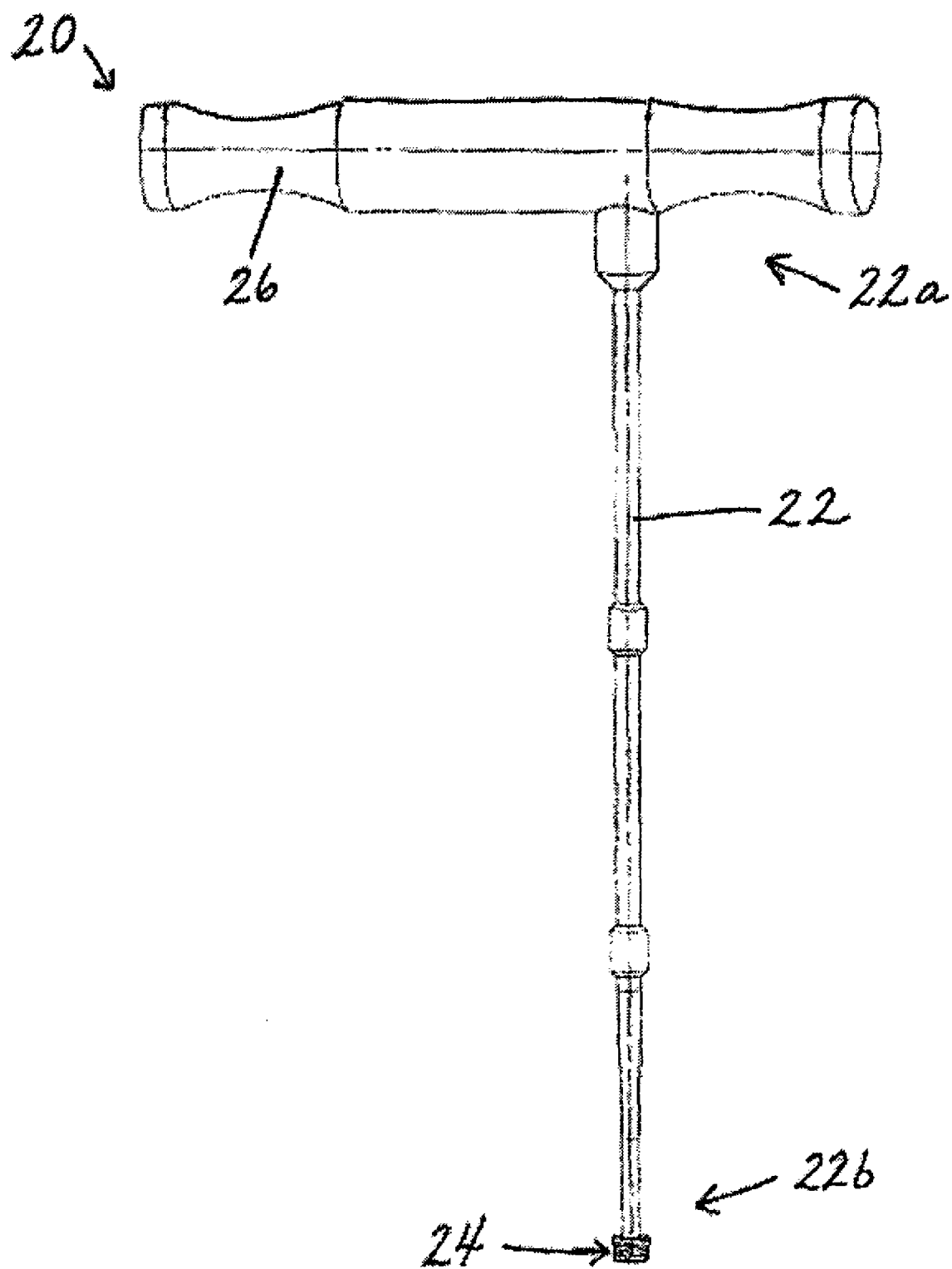
FIG. 2A is a perspective view of a removal tool according to one embodiment of the present invention.

Several techniques can be used to apply the predetermined force to the frangible portion 18 of the extension member 12. For example, a removal tool 20 can be inserted through a lumen 17 of the percutaneous access device 12 or extension member 12 and it can be actuated to apply a radially directed force to an inner surface 18c of the extension member 12 to break the extension member 12 away from the spinal anchor 14. A variety of configurations are available for the removal tool 20. FIG. 2A illustrates one exemplary removal tool 20 that generally includes an elongate member 22 having a proximal end 22a that is adapted to remain outside the body and a distal end 22b that is adapted to be inserted through the lumen 17 of the extension member 12 and to be positioned adjacent to the spinal anchor 14. The distal portion 22b can include an engagement mechanism 24 that is adapted to engage an inner surface 18c of the extension member 12 and to apply an outward or radially directed force to the extension member 12 disposed therearound to break at least a portion of the extension member 12 apart from the spinal anchor 14. The removal tool 20 can also include a handle 26 disposed on the proximal end 22a of the elongate member 22. The handle 26 can be used to manipulate the device, as will be discussed in more detail below.

Figure 2B:
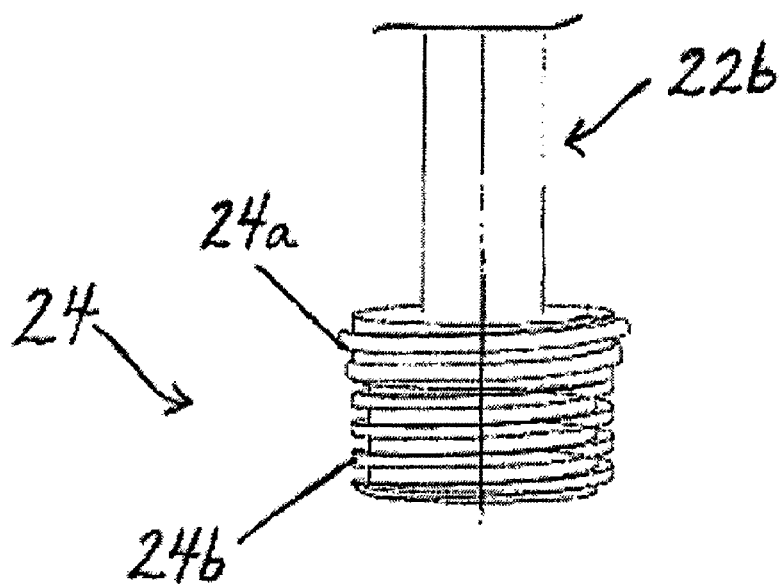
FIG. 2B is an enlarged perspective view of a distal end of the removal tool shown in FIG. 2A.
Figure 2C:
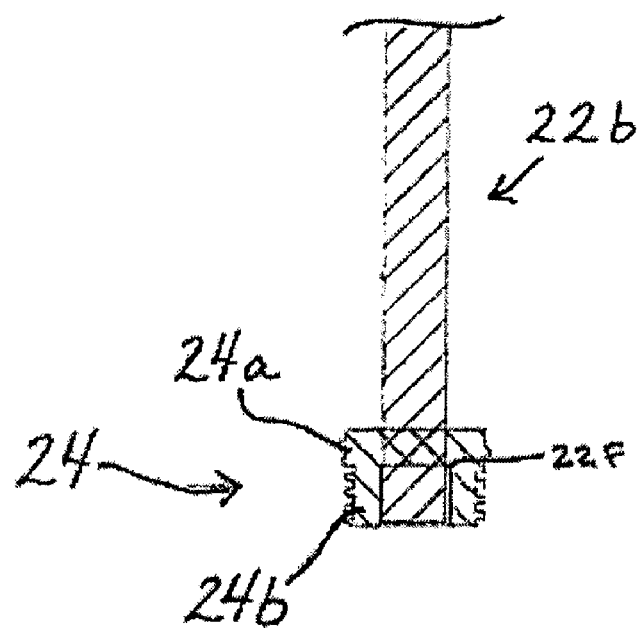
FIG. 2C is a cross-sectional view of the tool shown in FIG. 2B.

The engagement mechanism 24 can have a variety of configurations, and the size and shape of the engagement mechanism 24 can vary depending on the configuration of the extension member 12. For example, in the embodiment shown in FIGS. 2A-2C, the engagement mechanism 24 is in the form of a set screw or other threaded member formed on a distal portion 22b of the elongate member 22 and adapted to engage the complementary threads formed in the distal end of the extension portion 12. As shown in FIGS. 2B and 2C, the engagement mechanism 24 has a proximal threaded portion 24a with an outer diameter that is greater than an outer diameter of a distal threaded portion 24b. In other words, the thread on the proximal portion is oversized relative to the thread on the distal portion. The proximal threaded portion 24a can be sized to engage threads formed within the extension portion 12, and the distal threaded portion 24b can be configured to engage threads formed in the receiver member 16. FIG. 1B illustrates threads 12t formed on inner surface of the extension member 12 just proximal to the frangible portion 18, and threads 16t formed on an inner surface of the receiver member 16 just distal to the frangible portion 18. The proximal threaded portion 24a on the engagement mechanism 24 can also have a size that is configured to apply a radially directed force to the threads 12t on the extension member 12 to break the frangible portion 18 and thereby separate the extension member 12 from the receiver member 16. This can be achieved using various techniques. For example, a distal-most portion of the extension member 12, i.e., the portion located adjacent to or at the frangible portion 18, can be tapered such that the threaded portion 24a will apply a radially directed force thereto to cause the frangible portion 18 to break. Alternatively, the threads on the proximal threaded portion 24a can have an increasing diameter to cause the proximal threaded portion 24a to apply a radially directed force to the extension member 12. The distal threaded portion 24b, on the other hand, can have threads that complement the threads 16t within the receiver member 16 to allow the two portions to mate to one another. In use, the distal threaded portion 24b can thus function as a locking mechanism for locking a spinal connector, such as a spinal rod, within the receiver member 16.

The engagement mechanism 24, or a portion thereof, can also optionally be frangibly mated to the distal end 22b of the elongate member 22. This will allow the elongate member 22 to be detached from the engagement mechanism 24, thus allowing the engagement mechanism 24, or a portion thereof, to remain mated to the receiver member 16 of the anchor 14. The frangible portion can be formed at various locations on the removal tool 20. For example, FIG. 2C illustrates a frangible portion 22f formed within the engagement mechanism 24 at a location that is between the proximal and distal threaded portions 24a, 24b. In other embodiments, the proximal and distal threaded portions 24a, 24b can be frangibly mated to one another, thus allowing the proximal threaded portion 24a to be separated from the distal threaded portion 24b and removed from the body.

In use, the removal tool 20 can be actuated by inserting the elongate member 22 through the extension member 12 to position the engagement mechanism 24 within the distal end 12b of the extension member 12. The distal threaded portion 24b can pass through the threads 12t formed within the distal end 12b of the extension member 12, as they will have a size that is less than a size of the threads 12t formed within the extension member 12. The tool 20 can then be rotated with respect to the extension member 12, using, for example, the handle 26. As the tool 20 is rotated, the proximal threaded portion 24a will engage the threads 12t formed in the extension portion while the distal threaded portion 24b engages the threads 16t formed within the receiver member 16. Continued rotation will cause the proximal threaded portion 24a to apply a radially directed force to the extension member 12, thereby breaking the frangible portion 18 formed between the extension member 12 and the receiver member 16. The extension member 12 can thus be removed from the patient's body, leaving the spinal anchor 14 implanted in bone.

In another embodiment, the engagement mechanism can be in the form of a cam, wedge, or other inclined surface formed on a distal portion of an elongate shaft of a removal tool. FIGS. 3A-3C illustrate a distal end 22b' of an elongate shaft 22' of a removal tool having an engagement mechanism 24' in the form of a cam having first and second fins 30a', 30b' disposed on opposed sides of and extending radially outward from the shaft 22'. Each fin 30a', 30b' can have a length l that is configured to correspond to a width of the slots 13a, 13b formed in the arms 12c, 12d of the extension member 12 to allow the fins 30a', 30b' to be slidably received therein during insertion of the removal tool through the extension member 12. Each fin 30a', 30b' can also have height h that increases radially to form a ramped surface such that the fins 30a', 30b' can apply a radially directed force to the arms 12c, 12d of the extension member 12. In particular, after the tool is inserted to position the fins 30a', 30b' within the slots 13a, 13b and adjacent to the distal end of the extension member 12, as shown in FIGS. 3A and 3B, the removal tool can be rotated to cause the fins 30a', 30b' to move in between and into alignment with the arms 12c, 12d of the extension member 12, as shown in FIG. 3C. The increasing height h of each fin 30a', 30b' will apply a radially directed force to an inner surface 18c of each arm 12c, 12d, thereby causing the frangible portion to break thereby separating the extension member 12 from the receiver member 16 of the spinal anchor 14.

In another embodiment, the removal tool shown in FIGS. 3A-3C can include first and second arm members (not shown) that extend along the length of the elongate shaft. The fins can be rotated with respect to the first and second arm members to cause the fins to move in between and into alignment with the arm members. Similar to the removal tool described above, the increasing height of each fin will apply a radially directed force to an inner surface of each arm member, thereby causing the first and second arm members to apply a radially directed force to an inner surface of the extension member. The frangible portion will thus break thereby separating the extension member from the receiver member of the spinal anchor.

Figure 4A:
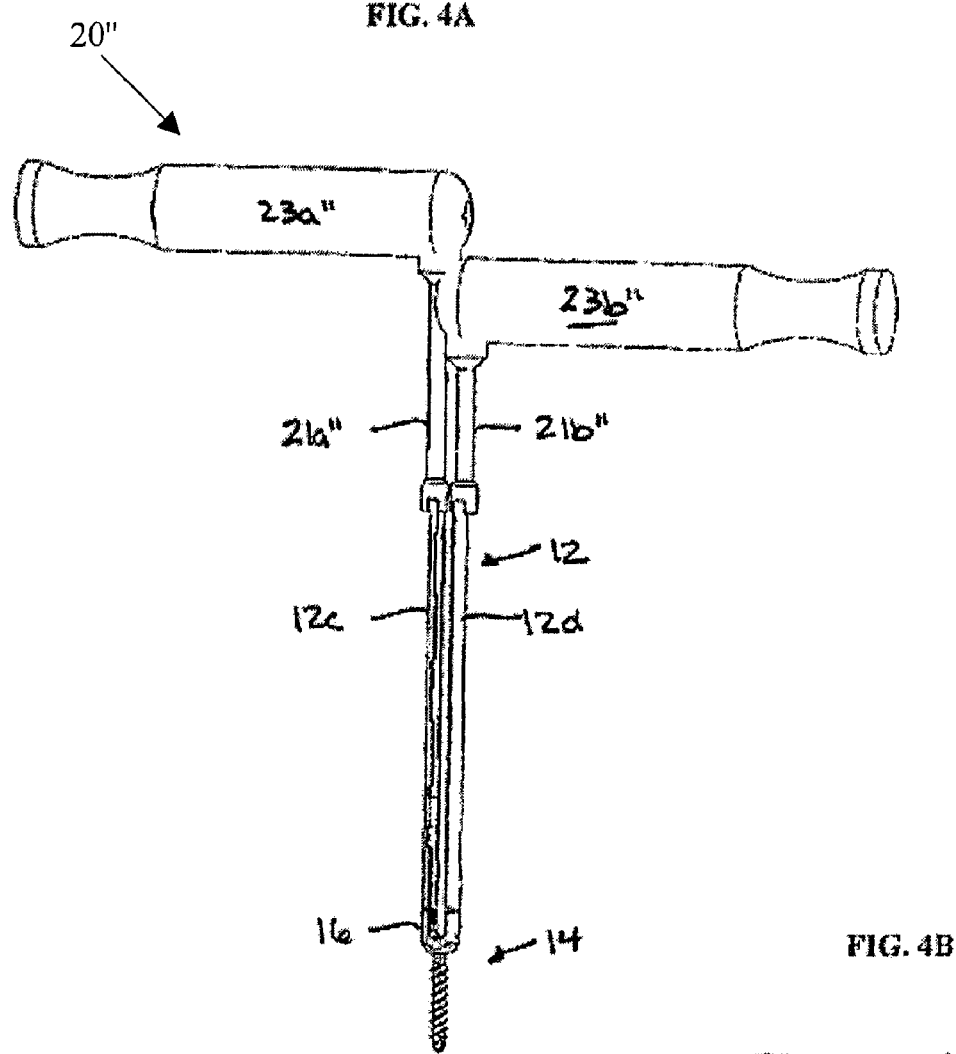
FIG. 4A is a perspective view of another embodiment of a removal tool having first and second breaker arms, showing the tool coupled to the device of FIG. 1A.
Figure 4B:
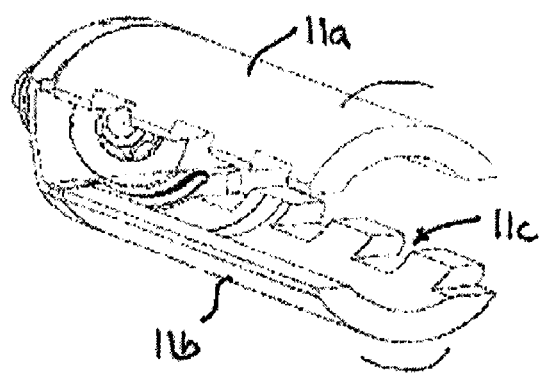
FIG. 4B is a perspective view of a distal portion of another embodiment of an extension member.

In another embodiment, shown in FIG. 4A, the removal tool 20" can include first and second breaker arms 21a", 21b" that are configured to engage the proximal end of the first and second arms 12c, 12d of the extension member 12. Various techniques can be used to engage the arms 12c, 12d, but as shown in FIG. 4A the breaker arms 21a", 21b" each include a U-shaped member for receiving a proximal end of the arms 12c, 12d on the extension member 12. Each breaker arm 21a", 21b" can also include a handle 23a", 23b" formed thereon, and once the breaker arms 21a", 21b" are engaged with the arms 12c, 12d on the extension member 12, the handles 23a", 23b" can be rotated in opposite directions to break the arms 12c, 12d of the extension member 12 away from the receiver member 16 of the spinal anchor 14. In another embodiment, in order to facilitate removal of the arms of the extension member, the arms can have complementary features formed therein that allow the arms to pass through one another. For example, FIG. 4B illustrates a distal end of first and second extension arms 11a, 11b having cut-outs 11c formed therein and offset from one another such that one arm, e.g., arm 11a, can pass through the other arm, e.g., arm 11b as the arms 11a, 11b are rotated by the breaker arms 21a", 21b".

Exemplary methods for implanting a spinal anchor 14 and delivering various tools and devices are also provided. In one exemplary embodiment, the procedure can begin by forming a minimally invasive percutaneous incision through tissue located adjacent to a desired implant site. The incision can be a relatively small incision having a length that is less than a diameter or width of the device being inserted therethrough, a spinal anchor and access device. Once the incision is made, a spinal anchor and access device, such as device 10, can be delivered to the anchor site. In particular, the anchor 14 can be inserted through the incision with the extension member 12 frangibly attached thereto and extending through the skin incision and outside of the patient's body. The bone-engaging member 14b of the anchor 14 can be driven into bone using a tool, such as a driver, that is passed through the extension member 12. While not shown, the extension member 12 can optionally include threads formed therein for mating with corresponding threads formed on the driver tool, thus facilitating advancement of the driver through the extension member 12 to drive the bone-engaging member 14b into bone. When the spinal anchor 14 is fully implanted, the bone-engaging member 14b will be fully disposed within bone and the receiver member 16 will be located adjacent to the bone such that it is either in contact with the bone or relatively close to the bone, i.e., 1 mm to 2 mm away from the bone. The extension member 12 will extend from the receiver member 16 and through the skin incision, thereby providing a pathway that spans through the skin incision to the anchor 14. Additional spinal anchor and access devices can be implanted in adjacent vertebrae using the same technique, or using other techniques known in the art.

Figure 5A:
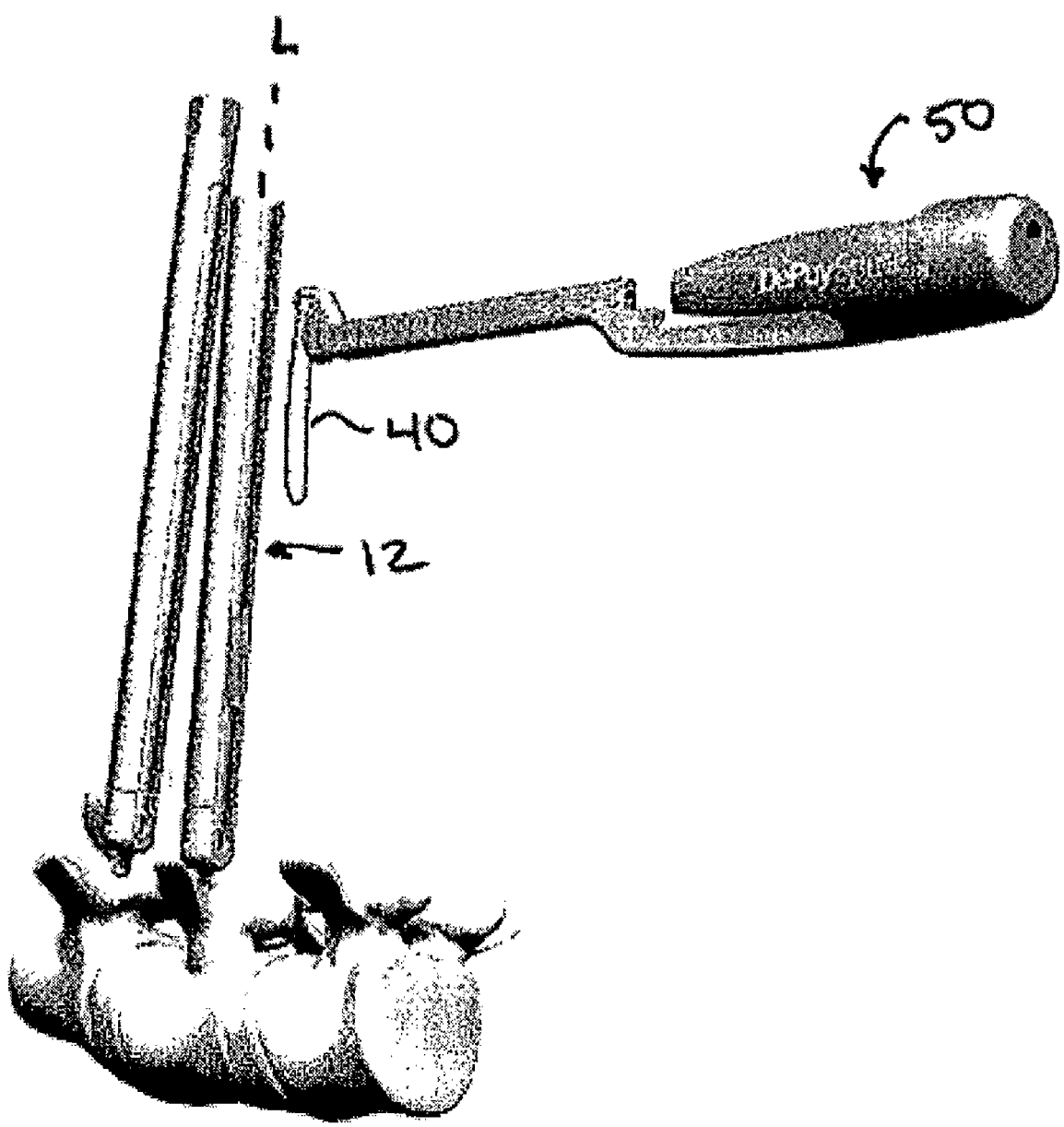
FIG. 5A is an illustration showing the device of FIG. 1A implanted in adjacent vertebra, and showing a spinal rod about to be inserted therethrough.
Figure 5B:
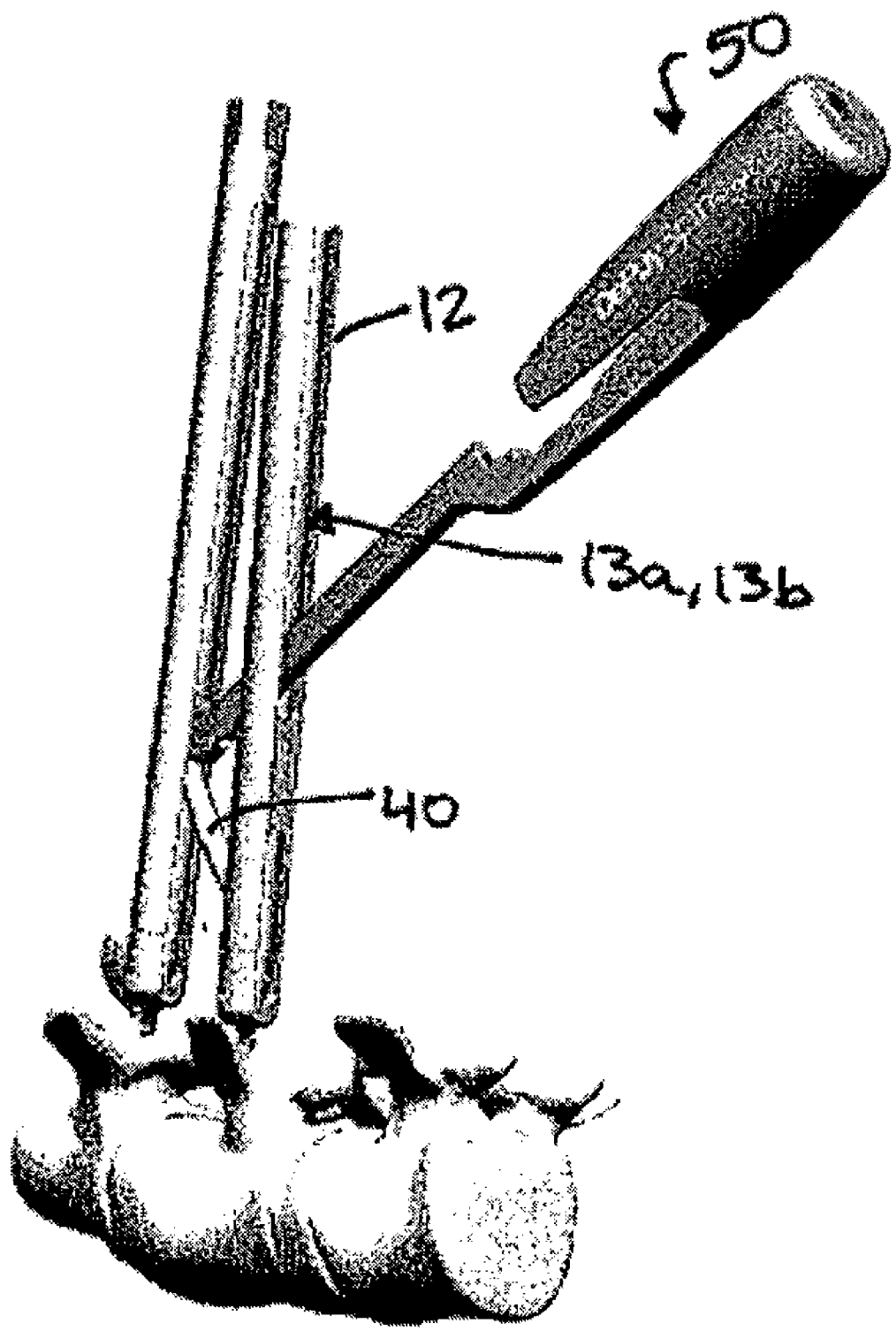
FIG. 5B is an illustration showing the spinal rod of FIG. 5A being passed through the slots in the extension members of the devices of FIG. 5A.
Figure 5C:
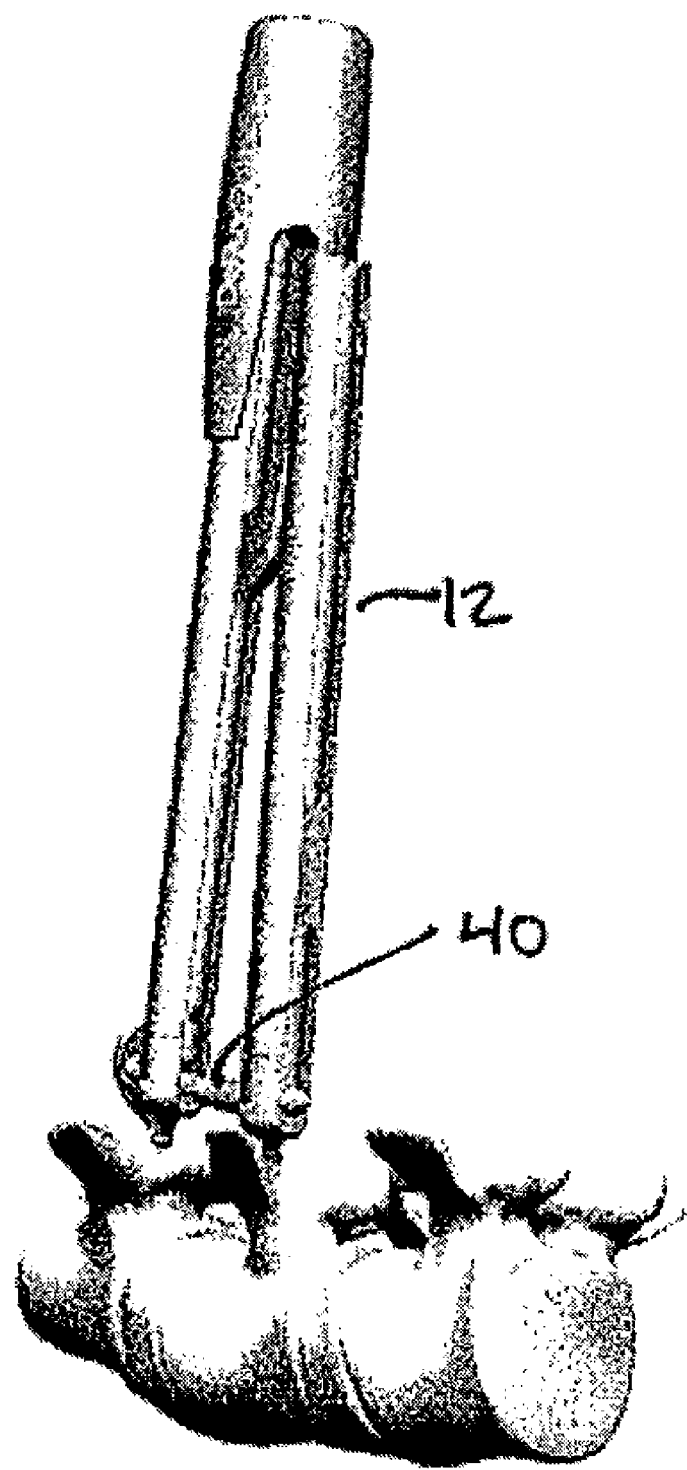
FIG. 5C illustrates the rod of FIG. 5B positioned within the spinal anchor of the devices of FIG. 5B.

Once the anchor 14 is implanted, the extension member 12 can be used to deliver various spinal connectors, fasteners, and other tools and devices to the implant site. For example, a spinal connector, such as a spinal rod, can be introduced through the extension member and positioned within the spinal anchor 14, and optionally within one or more additional spinal anchors implanted in adjacent vertebrae. FIGS. 5A-5C illustrate one exemplary method for inserting a spinal rod 40. The rod 40 is introduced through the extension member 12 in a first orientation, shown in FIG. 5A, in which the rod 40 is substantially parallel to the longitudinal axis of the extension member 12. The spinal rod 40 can then be manipulated to extend at an angle with respect to the first orientation, such that the rod 40 extends in a direction substantially transverse to the longitudinal axis L of the extension member 12, for example, in a direction that is substantially parallel to the patient's spine, as shown in FIG. 5C. Since the length of the spinal rod 40 will necessarily be greater than the inner diameter of the extension member 12, the slots 13a, 13b in the extension member 12 will allow the spinal rod 40 to pivot and pass therethrough while being transitioned from the first orientation to the second orientation, as shown in FIG. 5B. A person skilled in the art will appreciate that the exact position of the spinal rod 40 with respect to the longitudinal axis L of the extension member 12 will of course vary depending on the configuration of the spinal rod 40 or other spinal connector. As further shown in FIGS. 5A-5C, movement of the spinal rod 40 can be achieved using a manipulator or driver device 50. The manipulator device can have a variety of configurations, but it should be effective to allow controlled movement of the rod 40.

Figure 6A:
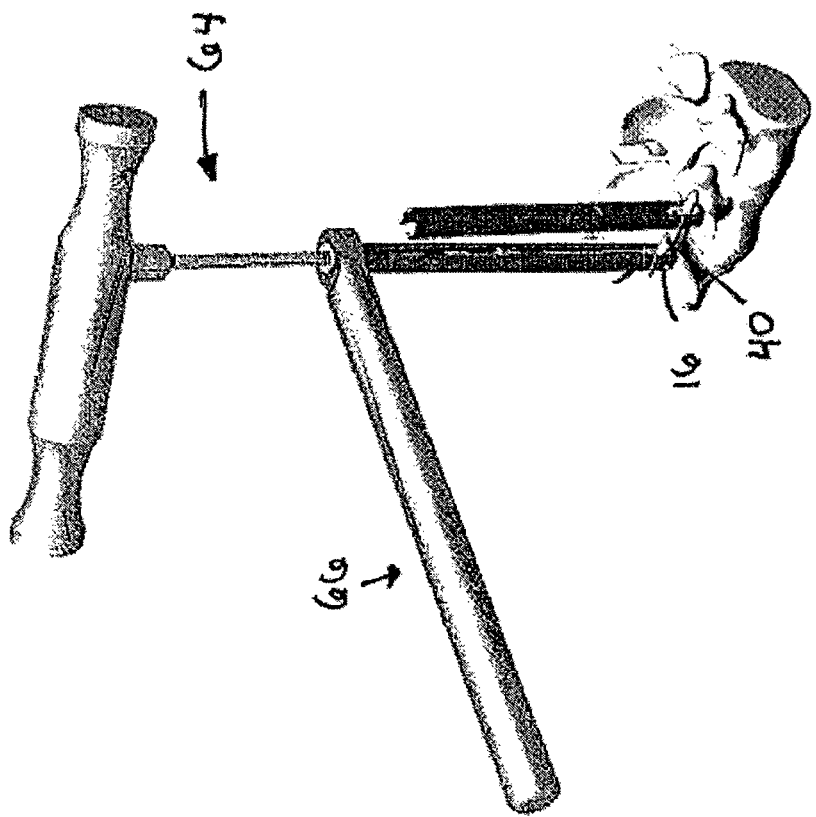
FIG. 6A is an illustration showing a driver tool being used to apply a fastening element to the spinal anchor of FIG. 5C to lock the rod within the anchor.
Figure 6B:
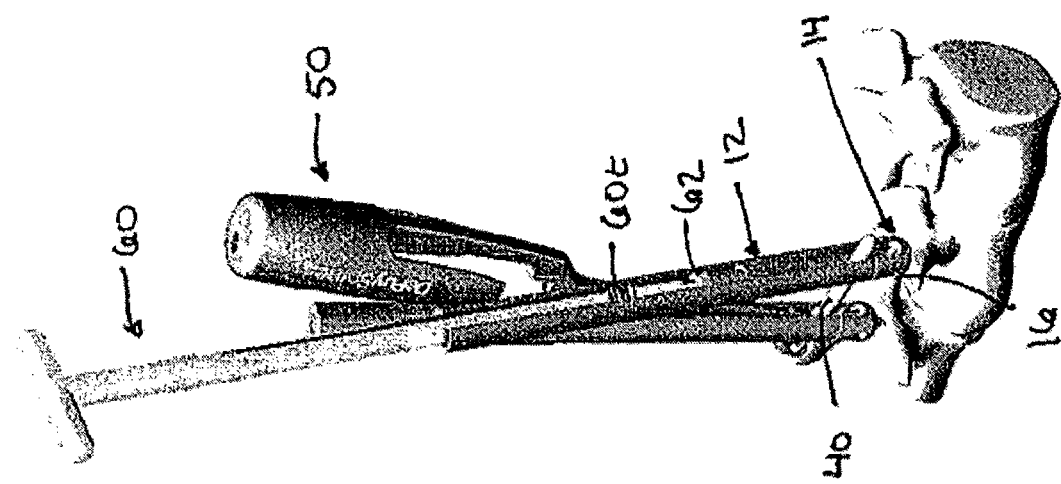
FIG. 6B is an illustration of one embodiment of a torque driver and a stabilizer to facilitate tightening of the fastening element of FIG. 6A.

Once the spinal rod 40 is properly positioned and fully seated in the receiver member 16, a closure mechanism or fastener can be inserted through the extension member 12 and applied to lock the rod 40 in place. A variety of closure mechanisms and tools for delivering closure mechanisms are known in the art, and they can be used with the present invention. By way of non-limiting example, FIG. 6A illustrates a driver tool 60 for delivering a set screw 62 to the spinal anchor 14 to lock the spinal rod 40 within the receiver member 16 of the spinal anchor 14. As shown, the set screw 62 is coupled to the distal end of the driver tool 60, which is passed through the inner lumen of the extension member 12. The illustrated driver tool 60 includes threads 60t formed on the shaft thereof for mating with corresponding threads (not shown) formed within the extension member 12. The threaded connection facilitates distal movement or advancement of the driver tool 60 through the extension member 12, thereby allowing the set screw 62 to reduce the rod 50 into the U-shaped recess in the receiver member 16. Final tightening of the set screw 62 can optionally be accomplished using a standard torque driver 64 along with a stabilizer 66 to prevent the receiver member 16 from rotating, as shown in FIG. 6B. The stabilizer 66 can interface with flats formed on the external surface of the extension member 12, as previously discussed with respect to FIG. 1F.

Figure 7A:
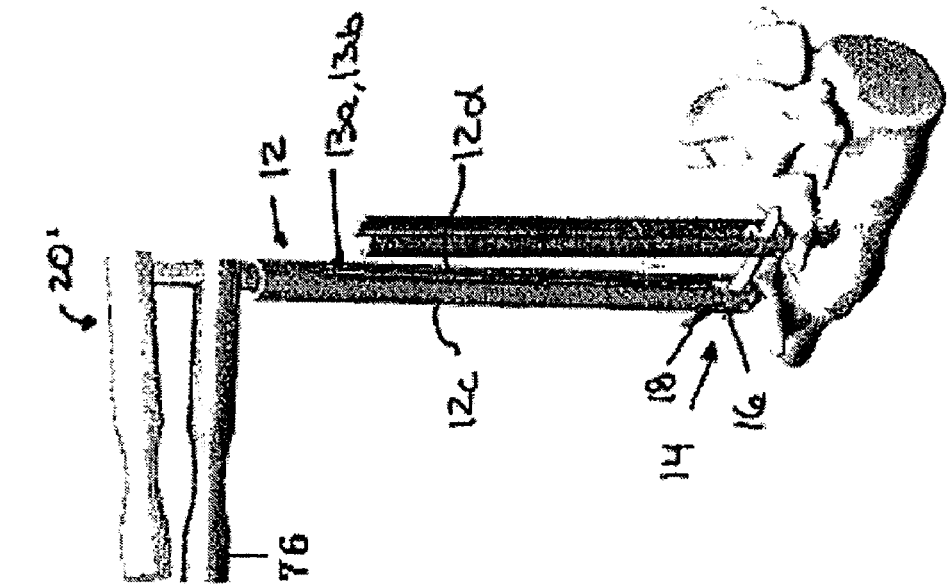
FIG. 7A is an illustration showing another embodiment of a technique for removing the extension arms from the spinal anchor of the device of FIG. 1A, showing a removal tool in an initial position.
Figure 7B:
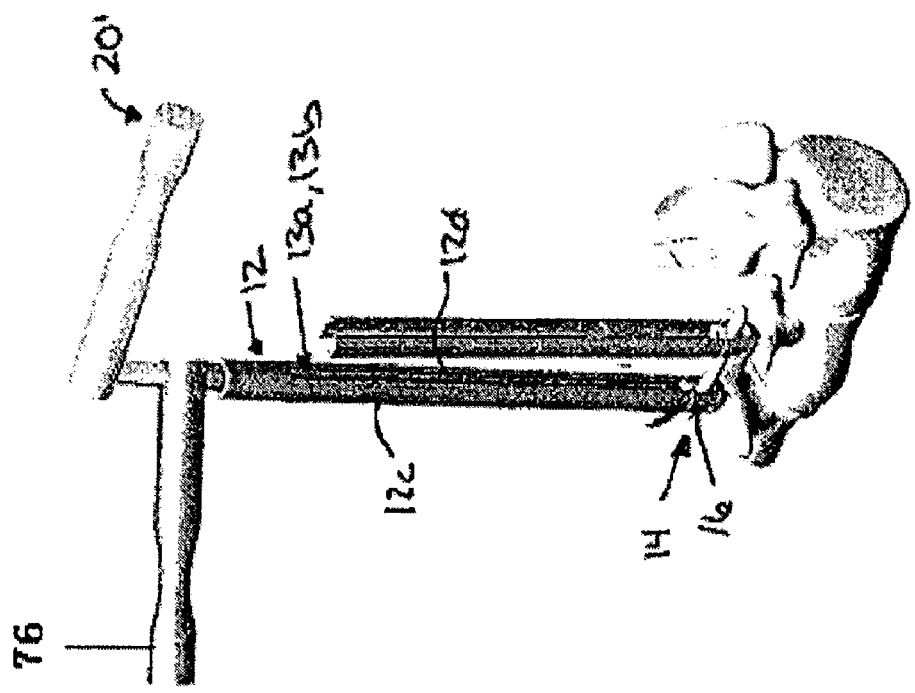
FIG. 7B is an illustration showing the removal tool of FIG. 7A in a final position.

While not shown, removal tool 20 previously described herein can optionally be used to deliver the engagement mechanism 24, which includes a distal threaded portion 24b that functions as a set screw. Once the engagement mechanism 24 is mated to the receiver member 16, the elongate member 22, and optionally the proximal threaded portion 24a of the engagement mechanism 24, can be frangibly detached from the distal threaded portion 24b to allow the removal tool 20 to be removed from the extension member 12 while the distal threaded portion 24b remains mated to the receiver member 16. This step can be repeated for adjacent spinal anchor(s). A person skilled in the art will appreciate that the spinal connector does not need to be directly attached to each anchor, and that it can be indirectly attached to the anchors using, for example, a band clamp, a slotted offset connector, or other techniques known in the art.

Where the removal tool is not configured to simultaneously deliver a fastening element while breaking the extension member 12 away from the receiver member 16, the extension member 12 can be detached from the anchor 14 by inserting a removal tool through the extension member 12 to apply a force to the frangible portion 18 formed between the extension member 12 and the spinal anchor 14. FIGS. 7A and 7B illustrate one exemplary method for breaking the extension member 12 away from the receiver member 16 of the spinal anchor 14 using the cam-type engagement mechanism 24' shown in FIGS. 3A-3C. As shown in FIGS. 7A and 7B, the removal tool 20' is passed through the extension member 12 to position the engagement mechanism (not shown) within the distal end of the extension member 12. The first and second fins on the engagement mechanism can be passed through the slots 13a, 13b formed in the extension member 12. The tool 20' is then rotated to cause the fins to pass between the arms 12c, 12d of the extension member 12, thereby applying a radially directed force to the arms 12c, 12d to break the frangible portion 18. The extension member 12 can thus be removed from the patient, leaving the spinal anchor 14 implanted in bone. As further shown in FIGS. 7A and 7B, a stabilizing tool 76 can optionally be passed through at least a portion of the extension member 12 for stabilizing the extension member 12 while the removal tool 20' is rotated.

Figure 8:
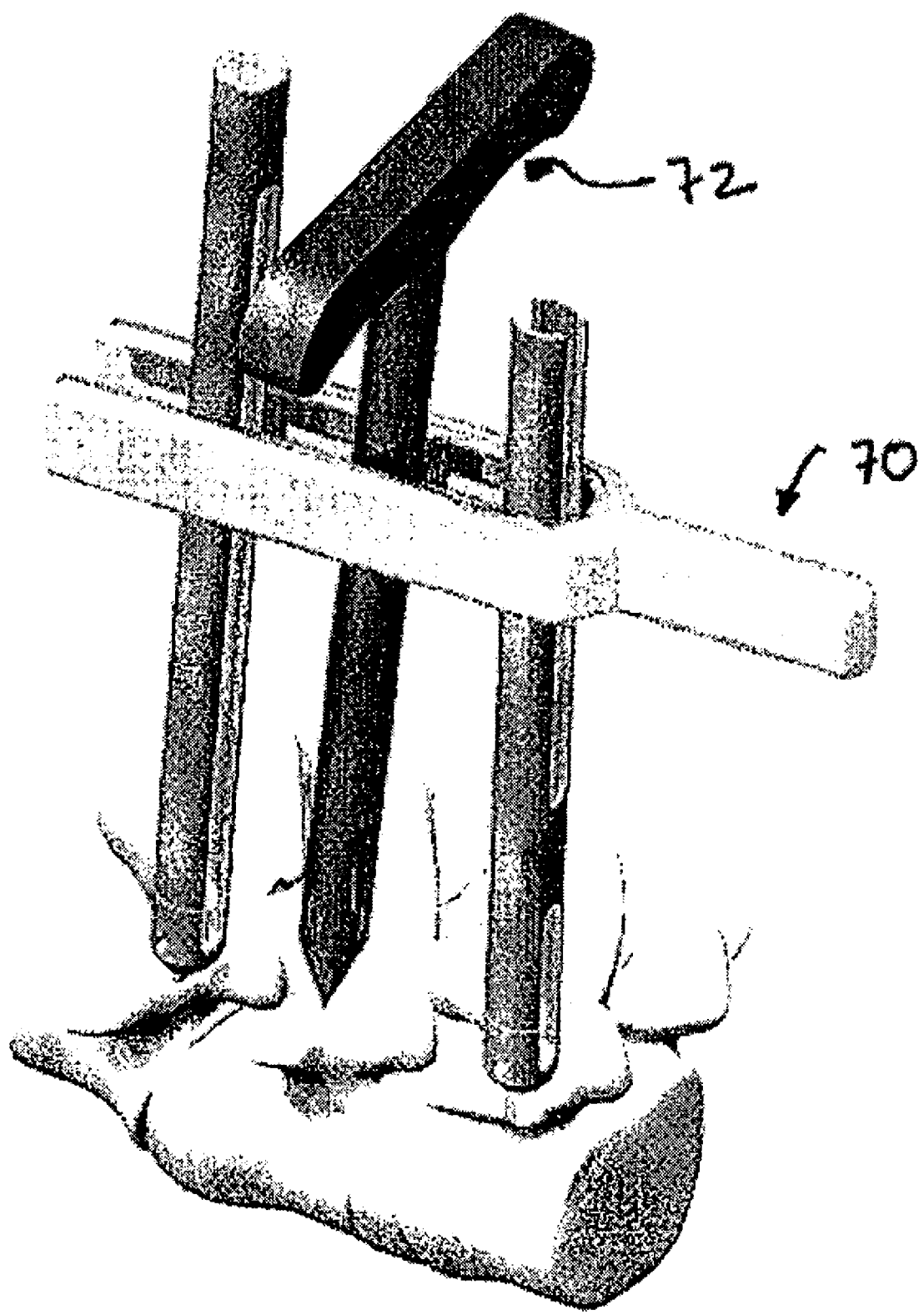
FIG. 8 is an illustration showing one embodiment of a jig and a targeting device in use with the spinal anchor and access device of FIG. 1A.
Figure 9:
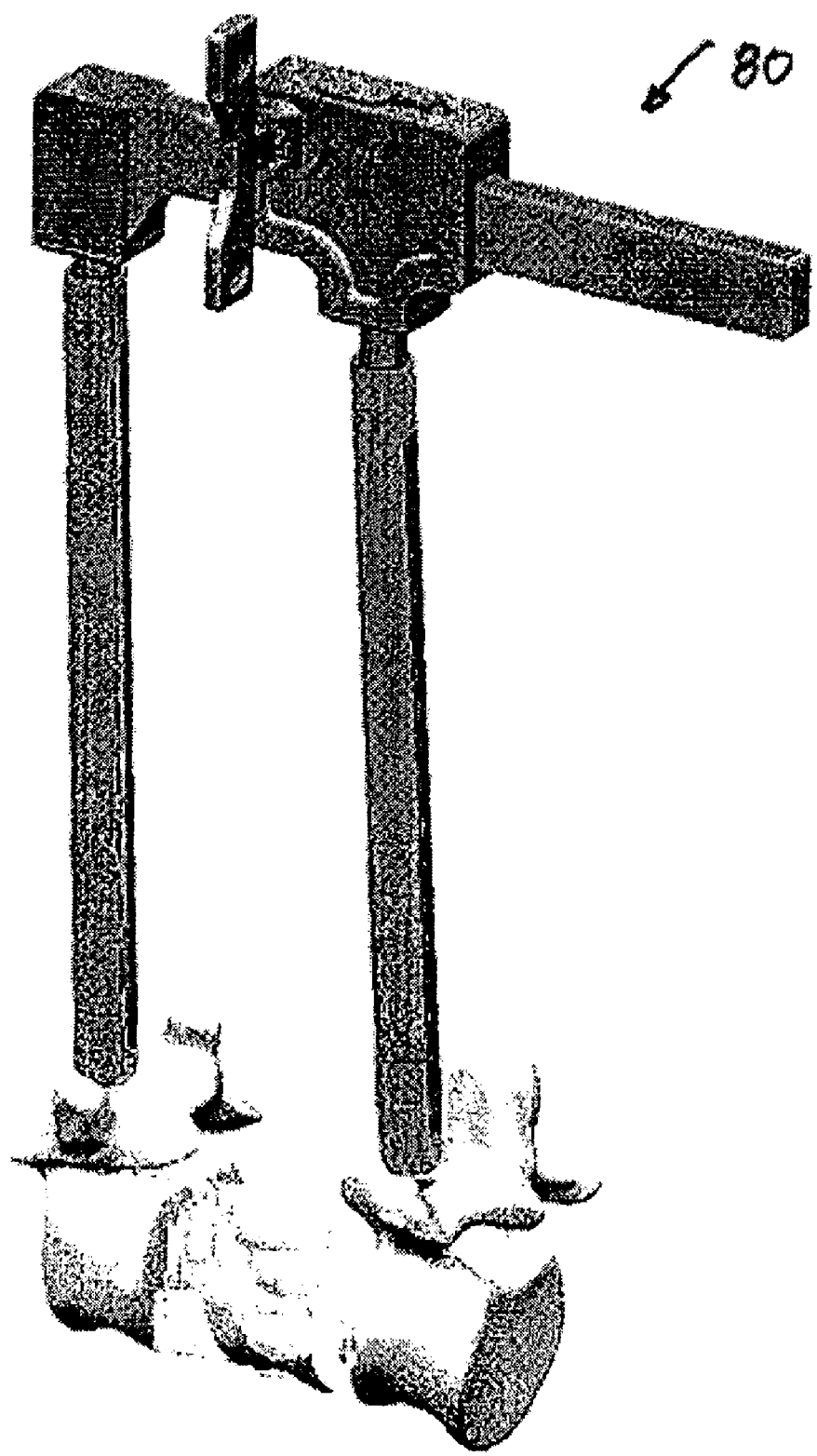
FIG. 9 is an illustration showing one embodiment of a distractor device in use with the spinal anchor and access device of FIG. 1A.
Figure 10:
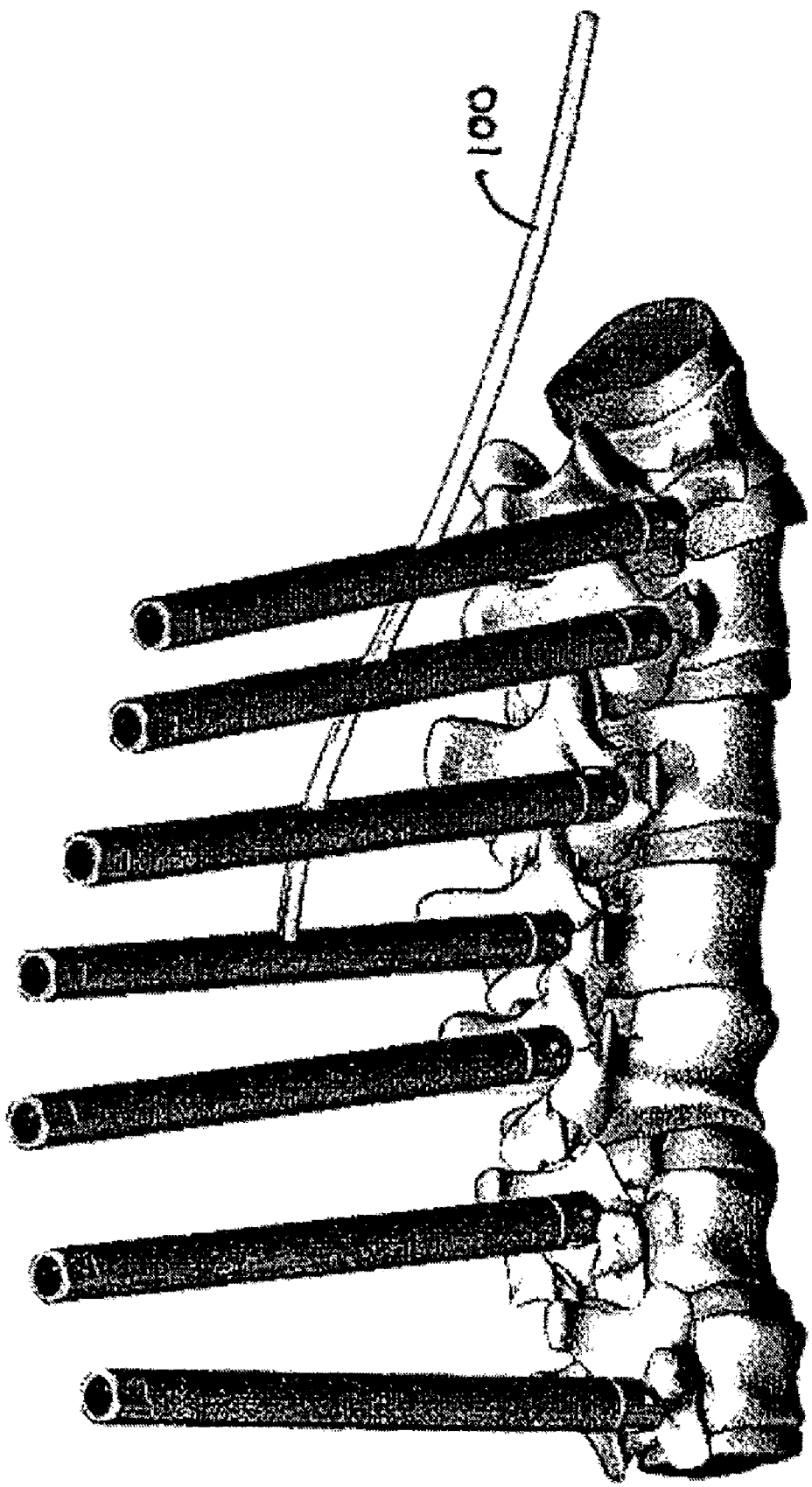
FIG. 10 is an illustration showing one embodiment of a technique for using the spinal anchor and access device of FIG. 1A to correct a spinal deformity.

In other embodiments, one or more spinal anchor and access devices can be implanted in adjacent vertebrae, and the extension member on each device can be used to perform other procedures, such as pedicle targeting, anchor alignment, distraction, deformity correction, etc. For example, the extension member 12 can also be used to manipulate the receiver member 16 coupled thereto. For example, the proximal end 12a of the extension member 12 can be grasped by a user and angularly oriented to thereby move the receiver member 16 relative to the bone-engaging member 14b. Where the anchor 14 is a monoaxial bone screw, movement of the extension member 12 will move the vertebra that the anchor 14 is implanted in. FIG. 8 illustrates a jig 70 mated to one or more extension members implanted in adjacent vertebrae. The jig 70 can be used, for example, to guide a pedicle targeting tool 72 and aid in the alignment of adjacent anchors. In yet another embodiment, as shown in FIG. 9, a distractor 80 can be mated to the extension member to facilitate the distraction of adjacent vertebrae. In another embodiment, shown in FIG. 10, multiple spinal anchor and access devices can be implanted in adjacent vertebrae and they can be used to correct a spinal deformity. For example, as shown in FIG. 10, the extension member of each device can aid in the placement of an extra long spinal rod 100, and insertion of the rod 100 through each extension member can move the extension members to thereby move the adjacent vertebrae into a desired orientation relative to one another. Separate instruments can optionally be used to further distract and/or manipulate the adjacent vertebrae. A person skilled in the art will appreciate that a variety of other tools and devices can be mated to and used in conjunction with the extension member disclosed herein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A removal tool, comprising:
   an elongate member having a proximal portion adapted to be positioned adjacent to a skin incision and a distal portion adapted to be positioned adjacent to a vertebra and to be received within a lumen formed in an extension member of a spinal anchor, the distal portion including a cam adapted to engage an inner surface of the extension member upon rotation thereof and to apply an outwardly directed force to the extension member disposed therearound to radially expand and break off at least a portion of the extension member apart from the spinal anchor.

2. The tool of claim 1, wherein the engagement mechanism comprises a set screw formed on the distal portion of the elongate member and having a proximal threaded portion with an outer diameter that is greater than an outer diameter of a distal threaded portion.

3. The tool of claim 1, further comprising a handle disposed on the proximal portion and adapted to rotate the elongate member to cause the cam to apply an outwardly directed force to an extension member disposed therearound.

4. The system of claim 1, wherein the cam includes first and second fins formed on opposite sides of the distal portion of the elongate member.

5. The system of claim 4, wherein the first and second fins increase in height radially and wherein rotation of the fins applies an outwardly directed linear force to an extension member of a spinal anchor.

6. A spinal system, comprising:
   a spinal anchor adapted to be implanted in bone and having a receiver member with a recess formed therein for seating a spinal connector, and an extension member frangibly coupled to the receiver member and adapted to span from a vertebra to a skin incision; and
   a removal tool having a cam formed on a distal end thereof adapted to engage an inner surface of the receiver member and to apply an outwardly directed force to an inner surface of the extension member to cause the extension member to break-away from the receiver member.

7. The system of claim 6, wherein the extension member comprises first and second opposed extension arms that extend proximally from the receiver member, and that are separated by at least one slot extending therebetween.

8. The system of claim 6, wherein the removal tool includes an elongate shaft and the cam is formed on a distal end of the elongate shaft.

9. The system of claim 8, wherein the engagement mechanism comprises a set screw having a proximal threaded portion with an outer diameter that is greater than an outer diameter of a distal threaded portion.

10. The system of claim 6, wherein the cam includes first and second fins formed on opposites sides of a distal end of the removal tool.

11. The system of claim 10, wherein the first and second fins increase in height radially and wherein rotation of the fins applies an outwardly directed linear force to the extension member of the spinal anchor.

12. The system of 6, wherein the cam is adapted to apply an outwardly directed force to radially expand and break off at least a portion of the extension member apart from the spinal anchor.

* * * * *